US011320902B2

(12) United States Patent
Lee et al.

(10) Patent No.: US 11,320,902 B2
(45) Date of Patent: *May 3, 2022

(54) SYSTEM AND METHOD FOR DETECTING INVISIBLE HUMAN EMOTION IN A RETAIL ENVIRONMENT

(71) Applicant: NURALOGIX CORPORATION, Toronto (CA)

(72) Inventors: Kang Lee, Toronto (CA); Pu Zheng, Toronto (CA)

(73) Assignee: NURALOGIX CORPORATION, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/875,322

(22) Filed: May 15, 2020

(65) Prior Publication Data
US 2020/0319706 A1 Oct. 8, 2020

Related U.S. Application Data

(63) Continuation of application No. 16/076,472, filed as application No. PCT/CA2017/050140 on Feb. 8, 2017, now Pat. No. 10,705,603.
(Continued)

(51) Int. Cl.
G06F 3/01 (2006.01)
A61B 5/16 (2006.01)
(Continued)

(52) U.S. Cl.
CPC ............. G06F 3/013 (2013.01); A61B 3/113 (2013.01); A61B 5/0077 (2013.01); A61B 5/145 (2013.01);
(Continued)

(58) Field of Classification Search
CPC ....... G06F 3/013; A61B 3/113; A61B 5/0077; A61B 5/145; A61B 5/1455; A61B 5/16;
(Continued)

(56) References Cited

U.S. PATENT DOCUMENTS 8,219,438 B1 7/2012 Moon et al.
10,705,603 B2 * 7/2020 Lee .................... G06Q 30/0201
(Continued)

FOREIGN PATENT DOCUMENTS

| CA | 2942852 A1 | 9/2014 |
| WO | 2015098977 A1 | 7/2015 |
| WO | 2016049757 A1 | 4/2016 |

OTHER PUBLICATIONS

International Search Report corresponding to PCT/CA2017/050140 dated May 15, 2017.
(Continued)

Primary Examiner — David F Dunphy
(74) Attorney, Agent, or Firm — Bhole IP Law; Anil Bhole; Marc Lampert

(57) ABSTRACT

A system for detecting invisible human emotion in a retail environment is provided. The system comprises a camera and an image processing unit. The camera is configured in a retail environment to capture an image sequence of a person before and during when a price of a product or service becomes visible. The image processing unit is trained to determine a set of bitplanes of a plurality of images in the captured image sequence that represent the hemoglobin concentration (HC) changes of the person, and to detect the person's invisible emotional states based on HC changes. The image processing unit is trained using a training set comprising a set of subjects for which emotional state is known.

15 Claims, 14 Drawing Sheets

Related U.S. Application Data

(60) Provisional application No. 62/292,574, filed on Feb. 8, 2016.

(51) Int. Cl.

| | | |
|---|---|---|
| *A61B 3/113* | (2006.01) | |
| *A61B 5/00* | (2006.01) | |
| *G06K 9/78* | (2006.01) | |
| *G06K 9/46* | (2006.01) | |
| *G06N 3/04* | (2006.01) | |
| *G06T 7/20* | (2017.01) | |
| *G06Q 30/02* | (2012.01) | |
| *A61B 5/145* | (2006.01) | |
| *A61B 5/1455* | (2006.01) | |
| *G06N 3/08* | (2006.01) | |
| *H04N 7/18* | (2006.01) | |
| *A61B 5/08* | (2006.01) | |
| *G06K 9/00* | (2022.01) | |
| *A61B 5/318* | (2021.01) | |

(52) U.S. Cl.
CPC .............. *A61B 5/1455* (2013.01); *A61B 5/16* (2013.01); *A61B 5/165* (2013.01); *G06K 9/4652* (2013.01); *G06K 9/78* (2013.01); *G06N 3/0445* (2013.01); *G06N 3/08* (2013.01); *G06Q 30/0201* (2013.01); *G06Q 30/0238* (2013.01); *G06T 7/20* (2013.01); *H04N 7/188* (2013.01); *A61B 5/08* (2013.01); *A61B 5/318* (2021.01); *A61B 2503/12* (2013.01); *G06F 2203/011* (2013.01); *G06K 9/00228* (2013.01); *G06K 9/00302* (2013.01); *G06T 2207/20081* (2013.01)

(58) Field of Classification Search
CPC ........ A61B 5/165; G06K 9/4652; G06K 9/78; G06N 3/0445; G06N 3/08; G06Q 30/0201; G06Q 30/0238; G06T 7/20; H04N 7/188

See application file for complete search history.

(56) References Cited

U.S. PATENT DOCUMENTS

| | | |
|---|---|---|
| 2005/0054935 A1 | 3/2005 | Rice et al. |
| 2006/0056509 A1 | 3/2006 | Suino et al. |
| 2007/0202477 A1 | 8/2007 | Nakagawa |
| 2009/0318773 A1 | 12/2009 | Jung et al. |
| 2012/0257035 A1 | 10/2012 | Larsen |
| 2014/0107439 A1 | 4/2014 | Asumori et al. |
| 2014/0336479 A1 | 11/2014 | Ando |
| 2014/0365272 A1 | 12/2014 | Hurewitz |

OTHER PUBLICATIONS

Jimenez et al. "A practical appearance model for dynamic facial color", ACM Trans. Graph., 29(6):I41:I—14I:I0, Dec. 2010.

Nguyen et al. "Investigating Brain Activity When Listening to Different Types of Music by Near-Infrared Spectroscopy", 29th Southern Biomedical Engineering Conference, 2013, pp. 83-86.

Ramirez et al. "Color Analysis of Facial Skin: Detection of Emotional State", 2014 IEEE Conference on Computer Vision and Pattern Recognition Workshops, Jun. 23-28, 2014 (Jun. 28, 2014), pp. 474-479.

Tsumura et al., "Image-based skin color and texture analysis/synthesis by extracting hemoglobin and melanin information in the skin", Proc. ACM Transactions on Graphics, SIGGRAPH 2003.

Wioleta, "Using Physiological Signals for Emotion Recognition", The 6th International Conference on Human System Interaction (HSI), Sopot, Poland, Jun. 6-8, 2013, pp. 556-561.

Written Opinion corresponding to PCT/CA2017/050140 dated May 15, 2017.

Yanushkevich et al.: "Decision-Making Support in Biometric-Based Physical Access Control Systems: Design Concept, Architecture, and Applications" In: "Biometrics", Oct. 26, 2009 (Oct. 26, 2009), pp. 599-631.

\* cited by examiner

From: December 1, 2015 00:00:00
To:    December 31, 2015 23:59:59

| Camera ID | Product ID | Image sequences captured | Mean emotional intensity score | Median emotional intensity score | Mean emotional bias | Median emotional bias |
|---|---|---|---|---|---|---|
| 1 | 49038135 | 1687 | 2.31 | 2.17 | 4.45 | 4.51 |
| 2 | 24103088 | 1823 | 1.97 | 1.99 | 4.64 | 4.69 |
| 3 | 12416561 | 1348 | 2.25 | 2.32 | -2.97 | -2.73 |
| 4 | 81342433 | 1193 | 2.17 | 2.31 | -3.17 | -3.32 |
| 5 | 13385164 | 1445 | 1.83 | 1.77 | 1.72 | 1.75 |
| 6 | 16513426 | 1379 | 2.42 | 2.45 | 3.71 | 3.60 |
| 7 | 65423624 | 1207 | 2.11 | 2.02 | 4.19 | 4.22 |

Fig. 10

SYSTEM AND METHOD FOR DETECTING INVISIBLE HUMAN EMOTION IN A RETAIL ENVIRONMENT

TECHNICAL FIELD

The following relates generally to market analytics and more specifically to an image-capture based system and method for detecting invisible human emotion in a retail environment.

BACKGROUND

The science or art of retail environments, pricing, and promotions is complex. Many factors can influence consumer spending and retention, including, but not limited to, store location and layout, staff behavior, cleanliness, product placement, presentation, pricing, and promotions. Each of these factors in isolation can somewhat readily be understood but, taken in combination, can be very difficult to balance in order to increase profits.

In order to better understand this problem, some retailers employ internal and external consultants that use a combination of science and experience to analyze the various factors that impact profits. While these consultants provide valuable information, they are still somewhat predictive rather than analytical. Their experience may cause them to predict how to optimize the factors in a manner that is not necessarily supported by reality. The cost of having such consultants revisit a retail location repeatedly with any regularity can outweigh the benefits. Further, the evaluation of any changes to the factors can be costly and slow.

Market analytics performed using sales data can provide some insight on a macro level, but, by itself, may not paint a full picture of the behaviors and decisions made by consumers. While consumers often have a logical basis for their shopping and purchasing behaviors, it can be difficult to understand what decisions they are making in the retail environment. Further, in other cases, there are less logical reasons for the shopping and purchasing behaviors of consumers that are hard to measure. Often, there are physiological responses that accompany such decisions and behaviours that are imperceptible by other humans.

SUMMARY

In one aspect, a system for detecting invisible human emotion in a retail environment within which a product is displayed in a product display to a person, is provided, the system comprising: a price display device for selectively displaying at least one price of the product, pursuant to a point of sale event; a camera configured to capture an image sequence of the person before and during the point of sale event; and a processing unit trained to determine a set of bitplanes of a plurality of images in the captured image sequence that represent the hemoglobin concentration (HC) changes of the person, to detect the person's invisible emotional states based on the HC changes, and to output the detected invisible emotional states, the processing unit being trained using a training set comprising HC changes of subjects with known emotional states.

In another aspect, a method for detecting invisible human emotion in a retail environment within which a product is displayed in a product display to a person, is provided, the method comprising: selectively displaying, by a price display device, at least one price of the product, pursuant to a point of sale event; capturing, by a camera, an image sequence of the person before and during the point of sale event; and determining, by a processing unit, a set of bitplanes of a plurality of images in the captured image sequence that represent the hemoglobin concentration (HC) changes of the person, detecting the person's invisible emotional states based on the HC changes, and outputting the detected invisible emotional states, the processing unit being trained using a training set comprising HC changes of subjects with known emotional states.

BRIEF DESCRIPTION OF THE DRAWINGS

The features of the invention will become more apparent in the following detailed description in which reference is made to the appended drawings wherein:

FIG. 10 is an exemplary report produced by the system;

DETAILED DESCRIPTION

Figure 1:
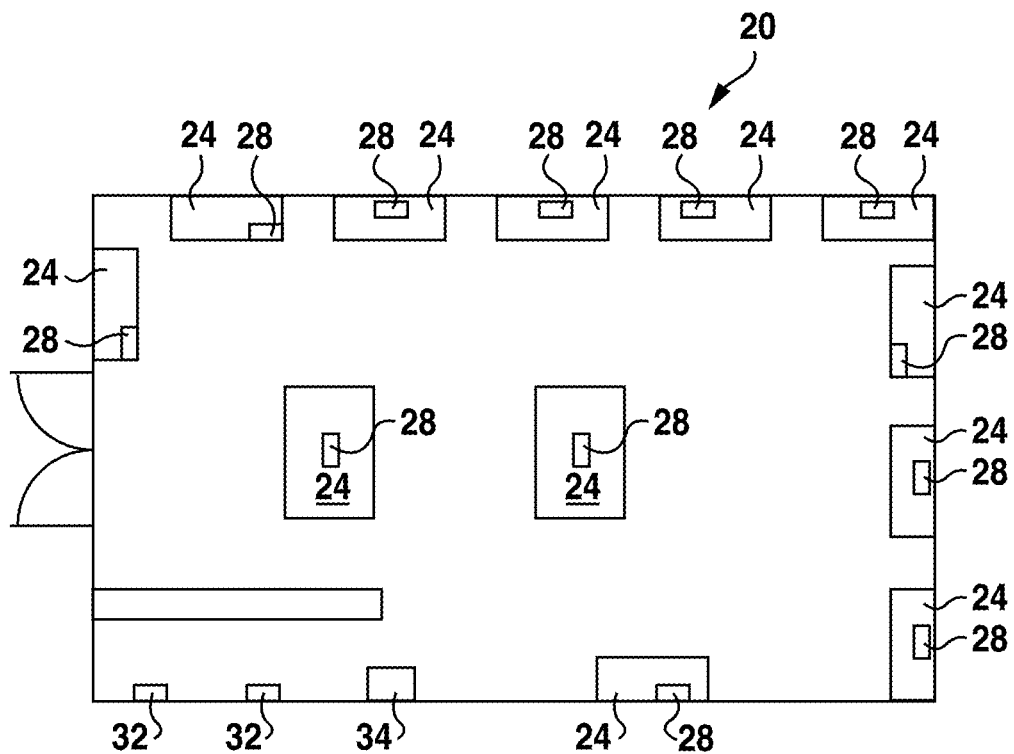
FIG. 1 is a schematic floor plan for a retail location employing a system for detecting invisible human emotion in accordance with an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to market analytics and more specifically to an image-capture based system and method for detecting invisible human emotion in a retail environment, and specifically the invisible emotional state of an individual captured in a series of images or a video. The system provides a remote and non-invasive approach by which to detect an invisible emotional state in a retail environment with a high confidence.

FIG. 1 shows a system 20 for detecting invisible human emotion in a retail environment in accordance with an embodiment. The retail environment has a set of product displays 24 upon which products are presented. The product displays 24 can be, for example, shelves upon which products are placed, product racks from which products are hung, etc. The system 20 comprises a set of price display devices 28 that are positioned within or adjacent the product displays 24. A pair of wall-mounted point-of-sale ("PoS") cameras 32 are configured to look at the face of a consumer when the consumer is positioned in front of a PoS register. A computer system 34 is in communication with the price display devices 24 and the PoS cameras 32 via a wired or wireless communication medium, such as Ethernet, Universal Serial Bus ("USB"), IEEE 802.11 ("W-Fi"), Bluetooth, etc.

Figure 2:
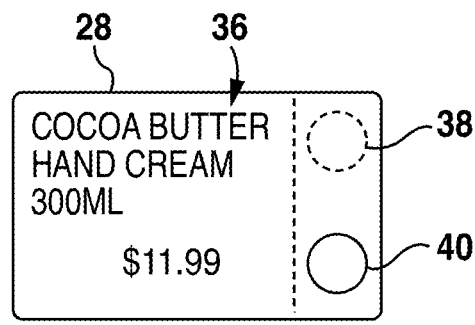
FIG. 2 is a front view of a price display unit of the system of FIG. 1 having a transdermal optical imaging camera.

Turning now to FIG. 2, one of the price display devices 28 is shown in greater detail. The price display device 28 has a display portion 36 that includes a display configured to be present product information and price for the products on the adjacent product display 24. The display can be any type of suitable display, such as, for example, LCD or LED. The price display device 28 also has a hidden or visible camera 38 that is configured to capture image sequences of consumers viewing the price display device 28. The camera 38 can be any suitable camera type for capturing an image sequence of a consumer's face, such as, for example, a CMOS or CCD camera. Memory in the price display device 28 enables storage of images captured until the images can be transferred to the computer system 34. Where the price display device 28 communicates wirelessly with the computer system 34, the price display device 28 includes a wireless radio of a suitable type. In the illustrated embodiment, the price display device 28 includes a Wi-Fi module for communicating with the computer system 34 via a wireless access point (not shown) with which the computer system 34 is in communication. A processor of the price display device 28 coordinates the capture of image sequences and their storage and transmission to the computer system 34. The price display device 28 can be wall-mounted, placed atop of a shelf, hung from a rack, etc., and may be powered by an internal battery, an external battery pack, coupling to an electrical outlet, etc.

The camera 38 can be configured with lenses to enable image capture from a wider angle, and the price display device 28 or the computer system 34 can be configured to transform the image sequences to compensate for any distortion introduced by the lenses.

A motion sensor 40 enables the detection of motion in the region in front of the price display device 28. The motion sensor 40 is configured to sense motion within a predetermined distance from the price display device 28.

The price display device 28 is configured to not display the price for the associated product until motion is detected by the motion sensor 40. Upon the detection of motion by the motion sensor 40, the price display device 28 examines images captured via the camera 38 to determine if it is likely that a face is detected in the captured images. If a face is detected, a point of sale event triggers pursuant to which the price display device 28 presents the price of the associated product while continuing to capture an image sequence via the camera 38. The captured image sequence for the period during which the face was detected is then transmitted to the computer system 34, along with an indication of when in the image sequence the price was displayed and an identifier of the price display device 28.

In other embodiments, the price display device 28 can transmit the image sequence for a predefined period prior to and after presentation of the price to the computer system 34.

In other embodiments, the price display device 28 can present the price of the associated product continuously rather than merely during point of sale events, and can transmit image sequences to the computer system 34 in which faces are detected. In other embodiments, the price display device 28 can continuously transmit the image sequences as they are being captured to the computer system 34. The price presented by the price display device 28 can be a static printed display in some embodiments.

The objects/products around each camera, and its location, can be registered with the computer system. The computer system 34 can then use gaze tracking to analyze the image streams to determine what the consumer was looking at during the image sequence to identify what the consumer is reacting to. In this manner, each camera can register invisible emotion detected for consumers in response to more than one possible stimulus. This stimulus may, for example, be actual product. In this regard, the computer system 34 is configured to determine the physiological response of the consumer at the time that the consumer laid eyes upon a particular product.

The PoS cameras 32 capture and communicate a continuous image sequence to the computer system 34. In this manner, consumer reactions to point of sale events such as being notified of a total or of any discounts can be registered and analyzed.

Figure 15:
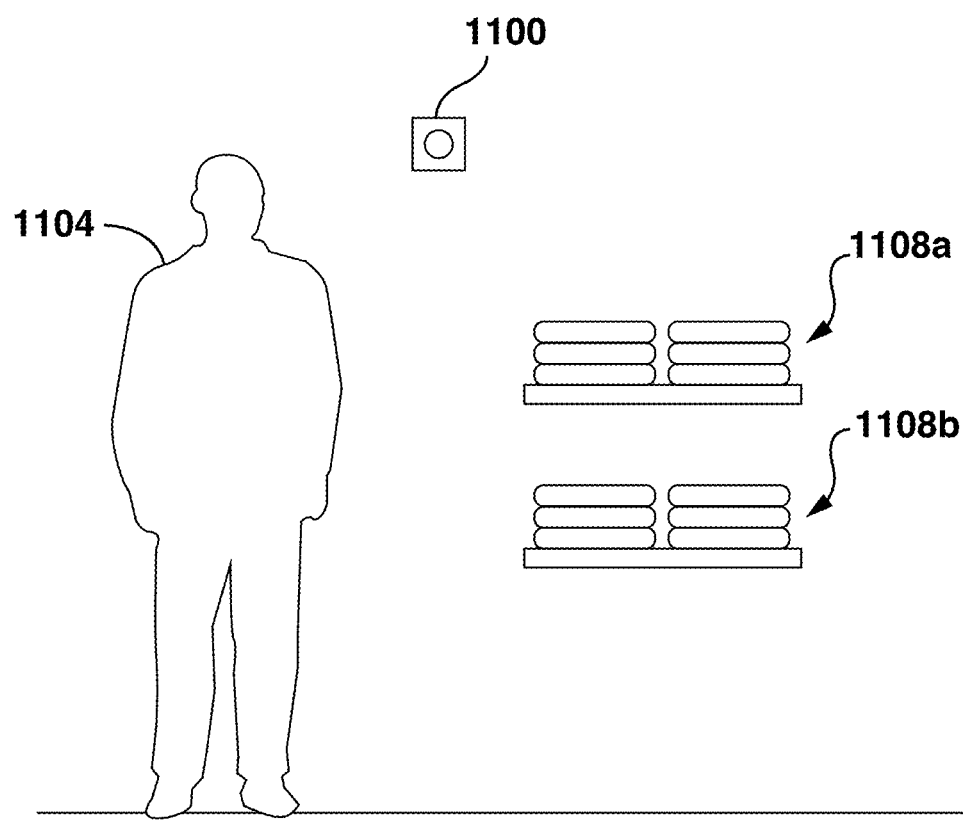
FIG. 15 illustrates a camera for detecting invisible human emotion in accordance with another embodiment.

In another configuration in accordance with another embodiment shown in FIG. 15, one or more separate cameras, such as camera 1100, are placed in various locations, such as on walls, shelves, ceiling, etc. of the retail location, and configured to capture image sequences and transmit them to the computer system continuously. The location of the cameras and their presence may be obscured or hidden to diminish the emotional impact of their presence on consumers. The cameras can be coupled with a motion sensor and can be configured to send image sequences to the computer system when motion is detected by the motion sensor. The camera 1100 is configured to capture image sequences of consumers in the retail location adjacent a mannequin 1104 displaying an outfit and a set of shelves 1108a, 1108b upon which sweaters are folded. The locations of the mannequin 1104 and the shelves 1108a, 1108b relative to the camera 1100 are registered with the computer system. Gaze tracking is employed by the computer system to determine if a consumer is viewing the mannequin 1104 or a particular one of the shelves 1108a, 1108b when an invisible human emotion is detected. Upon detecting an invisible human emotion in an image sequence received from the camera 1100.

Figure 4:
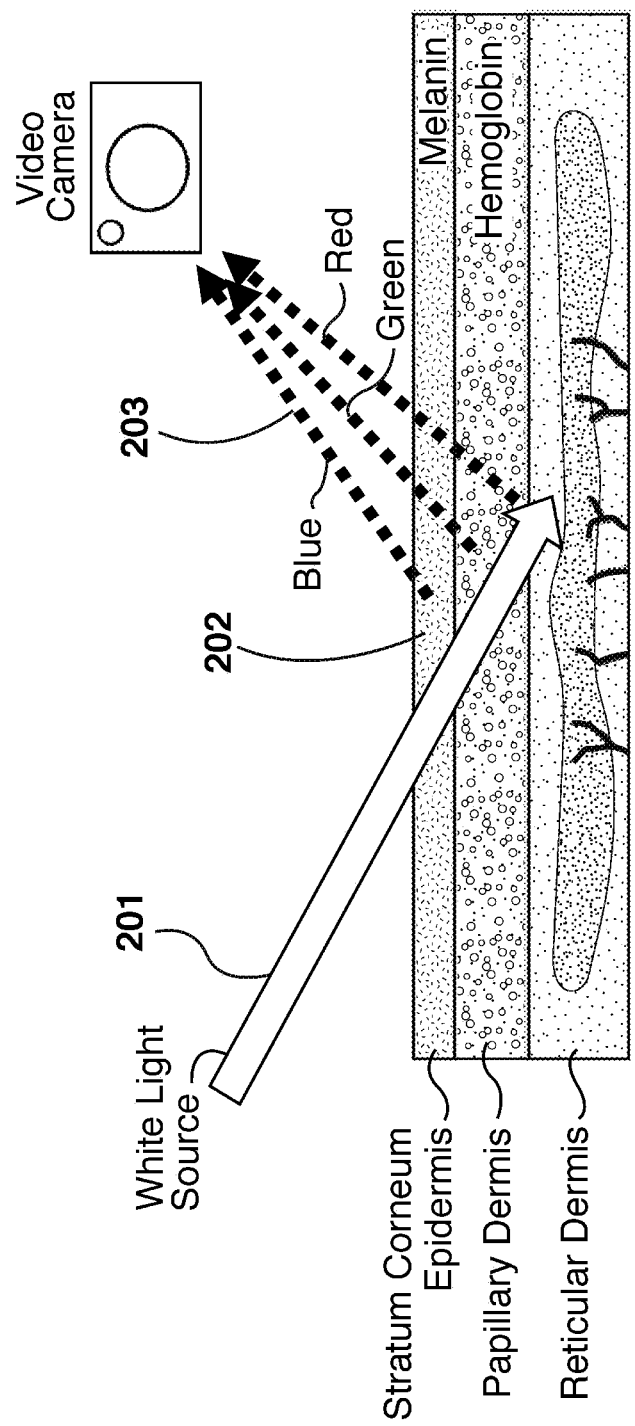
FIG. 4 illustrates re-emission of light from skin epidermal and subdermal layers.
Figure 5:
FIG. 5 is a set of surface and corresponding transdermal images illustrating change in hemoglobin concentration associated with invisible emotion for a particular human subject at a particular point in time.
Figure 6:
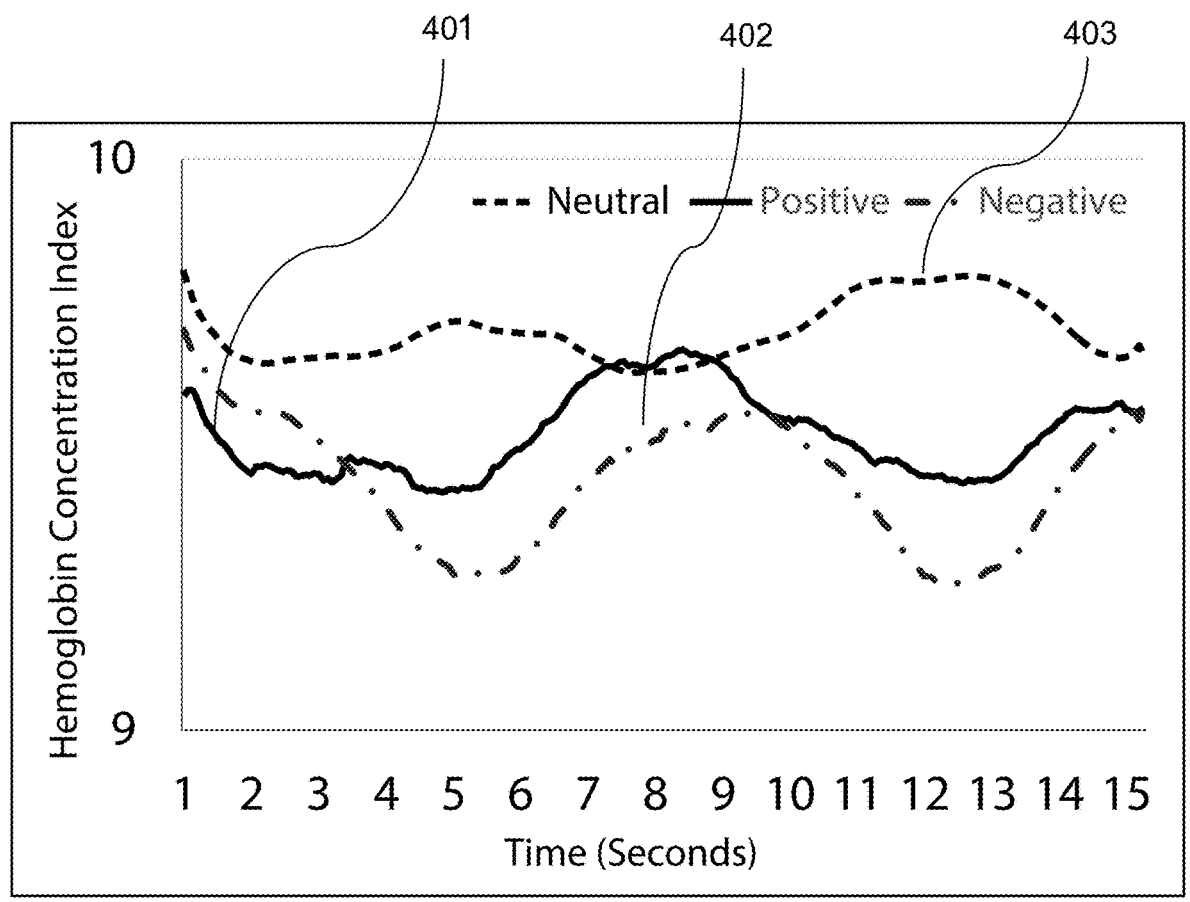
FIG. 6 is a plot illustrating hemoglobin concentration changes for the forehead of a subject who experiences positive, negative, and neutral emotional states as a function of time (seconds)

Hemoglobin concentration (HC) can be isolated from raw images taken from the camera 38, and spatial-temporal changes in HC can be correlated to human emotion. Referring now to FIG. 4, a diagram illustrating the re-emission of light from skin is shown. Light (201) travels beneath the skin (202), and re-emits (203) after travelling through different skin tissues. The re-emitted light (203) may then be captured by optical cameras. The dominant chromophores affecting the re-emitted light are melanin and hemoglobin. Since melanin and hemoglobin have different color signatures, it has been found that it is possible to obtain images mainly reflecting HC under the epidermis as shown in FIG. 5.

The system 20 implements a two-step method to generate rules suitable to output an estimated statistical probability that a human subject's emotional state belongs to one of a plurality of emotions, and a normalized intensity measure of such emotional state given a video sequence of any subject. The emotions detectable by the system correspond to those for which the system is trained.

Figure 3:
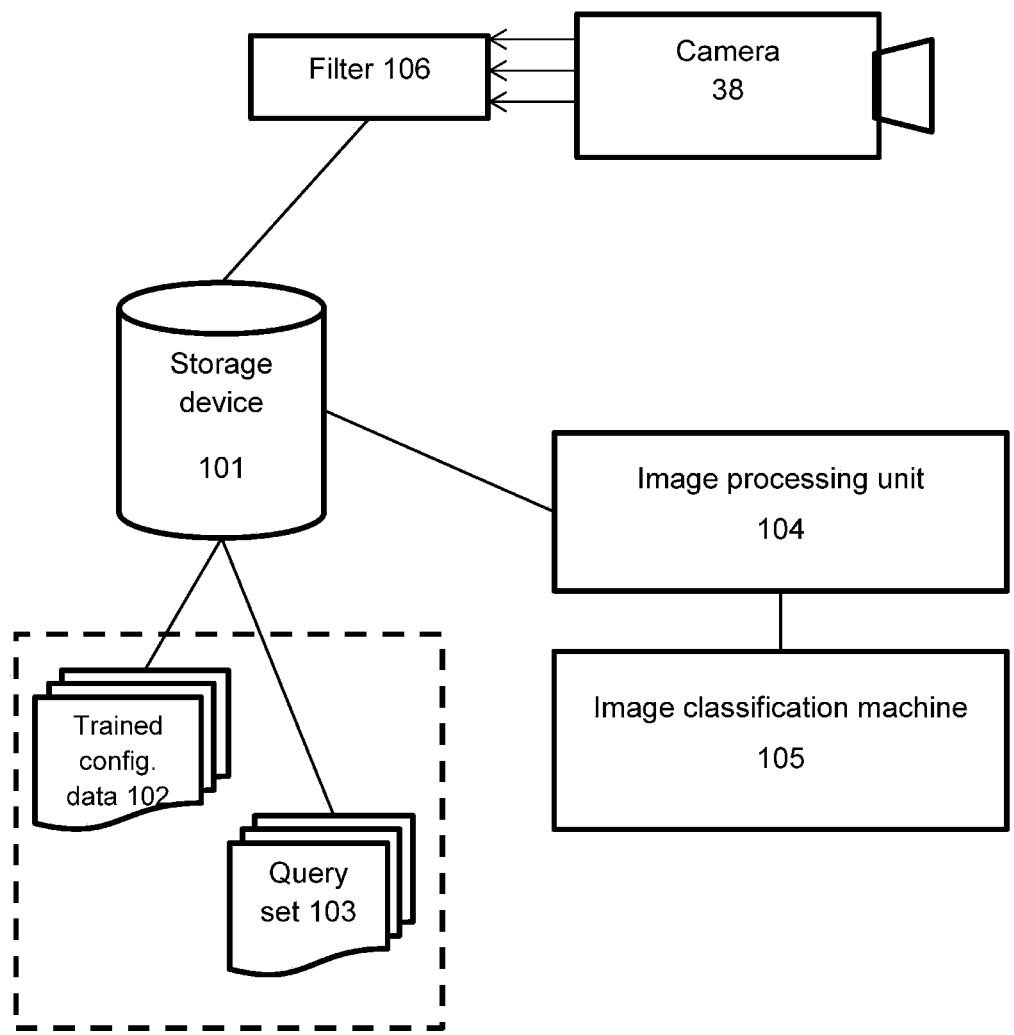
FIG. 3 is an block diagram of various components of the system for invisible emotion detection of FIG. 1.

Referring now to FIG. 3, various components of the system 20 for invisible emotion detection in a retail environment are shown in isolation. The computer system 34 comprises an image processing unit 104, an image filter 106, an image classification machine 105, and a storage device 101. A processor of the computer system 34 retrieves computer-readable instructions from the storage device 101 and executes them to implement the image processing unit 104, the image filter 106, and the image classification machine 105, The image classification machine 105 is configured with training configuration data 102 derived from another computer system trained using a training set of images and is operable to perform classification for a query set of images 103 which are generated from images captured by the camera 38, processed by the image filter 106, and stored on the storage device 102.

The sympathetic and parasympathetic nervous systems are responsive to emotion. It has been found that an individual's blood flow is controlled by the sympathetic and parasympathetic nervous system, which is beyond the conscious control of the vast majority of individuals. Thus, an individual's internally experienced emotion can be readily detected by monitoring their blood flow. Internal emotion systems prepare humans to cope with different situations in the environment by adjusting the activations of the autonomic nervous system (ANS); the sympathetic and parasympathetic nervous systems play different roles in emotion regulation with the former regulating up fight-flight reactions whereas the latter serves to regulate down the stress reactions. Basic emotions have distinct ANS signatures. Blood flow in most parts of the face such as eyelids, cheeks and chin is predominantly controlled by the sympathetic vasodilator neurons, whereas blood flowing in the nose and ears is mainly controlled by the sympathetic vasoconstrictor neurons; in contrast, the blood flow in the forehead region is innervated by both sympathetic and parasympathetic vasodilators. Thus, different internal emotional states have differential spatial and temporal activation patterns on the different parts of the face. By obtaining hemoglobin data from the system, facial hemoglobin concentration (HC) changes in various specific facial areas may be extracted. These multidimensional and dynamic arrays of data from an individual are then compared to computational models based on normative data to be discussed in more detail below. From such comparisons, reliable statistically based inferences about an individual's internal emotional states may be made. Because facial hemoglobin activities controlled by the ANS are not readily subject to conscious controls, such activities provide an excellent window into an individual's genuine innermost emotions.

Figure 9:
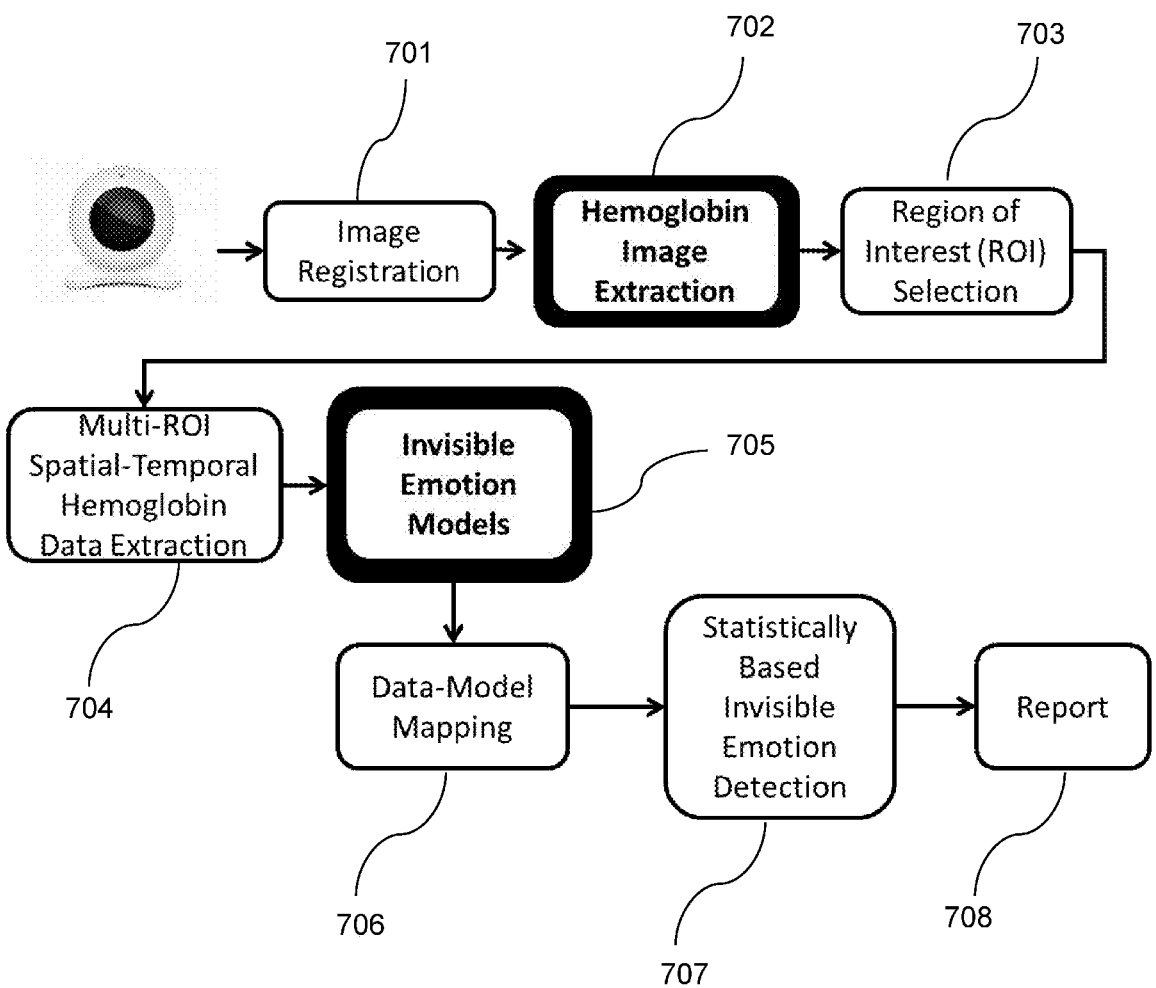
FIG. 9 is a flowchart illustrating a fully automated transdermal optical imaging and invisible emotion detection system.
Figure 13:
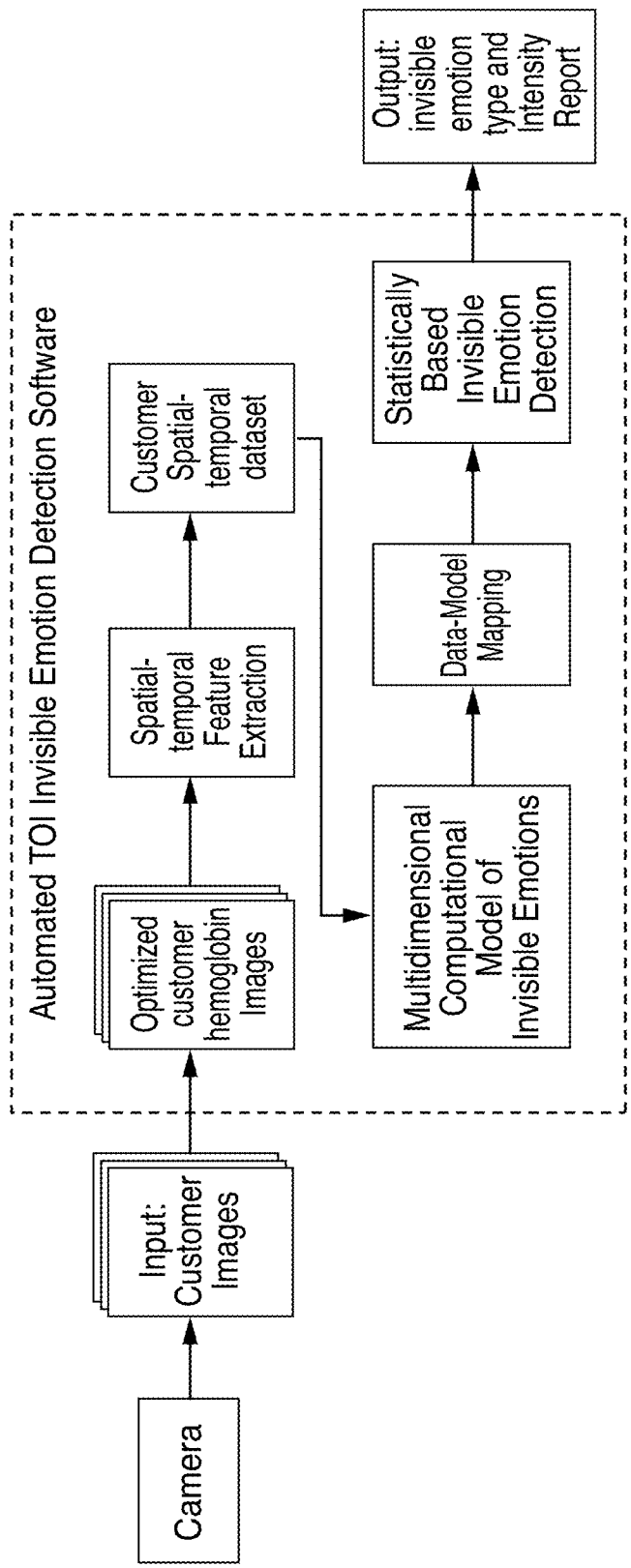
FIG. 13 is an illustration of an automated invisible emotion detection system.

Referring now to FIG. 9, a flowchart illustrating the method of invisible emotion detection performed by the system 20 is shown. The system 20 performs image registration 701 to register the input of a video/image sequence captured of a subject with an unknown emotional state, hemoglobin image extraction 702, ROI selection 703, multi-ROI spatial-temporal hemoglobin data extraction 704, invisible emotion model 705 application, data mapping 706 for mapping the hemoglobin patterns of change, emotion detection 707, and report generation 708. FIG. 13 depicts another such illustration of automated invisible emotion detection system.

The image processing unit obtains each captured image or video stream from each camera and performs operations upon the image to generate a corresponding optimized HC image of the subject. The image processing unit isolates HC in the captured video sequence. In an exemplary embodiment, the images of the subject's faces are taken at 30 frames per second using the camera. It will be appreciated that this process may be performed with alternative digital cameras and lighting conditions.

Isolating HC is accomplished by analyzing bitplanes in the video sequence to determine and isolate a set of the bitplanes that provide high signal to noise ratio (SNR) and, therefore, optimize signal differentiation between different emotional states on the facial epidermis (or any part of the human epidermis). The determination of high SNR bitplanes is made with reference to a first training set of images constituting the captured video sequence, coupled with EKG, pneumatic respiration, blood pressure, laser Doppler data from the human subjects from which the training set is obtained. The EKG and pneumatic respiration data are used to remove cardiac, respiratory, and blood pressure data in the HC data to prevent such activities from masking the more-subtle emotion-related signals in the HC data. The second step comprises training a machine to build a computational model for a particular emotion using spatial-temporal signal patterns of epidermal HC changes in regions of interest ("ROIs") extracted from the optimized "bitplaned" images of a large sample of human subjects.

For training, video images of test subjects exposed to stimuli known to elicit specific emotional responses are captured. Responses may be grouped broadly (neutral, positive, negative) or more specifically (distressed, happy, anxious, sad, frustrated, intrigued, joy, disgust, angry, surprised, contempt, etc.). In further embodiments, levels within each emotional state may be captured. Preferably, subjects are instructed not to express any emotions on the face so that the emotional reactions measured are invisible emotions and isolated to changes in HC. To ensure subjects do not "leak" emotions in facial expressions, the surface image sequences may be analyzed with a facial emotional expression detection program. EKG, pneumatic respiratory, blood pressure, and laser Doppler data may further be collected using an EKG machine, a pneumatic respiration machine, a continuous blood pressure machine, and a laser Doppler machine and provides additional information to reduce noise from the bitplane analysis, as follows.

ROIs for emotional detection (e.g., forehead, nose, and cheeks) are defined manually or automatically for the video images. These ROIs are preferably selected on the basis of knowledge in the art in respect of ROIs for which HC is particularly indicative of emotional state. Using the native images that consist of all bitplanes of all three R, G, B channels, signals that change over a particular time period (e.g., 10 seconds) on each of the ROIs in a particular emotional state (e.g., positive) are extracted. The process may be repeated with other emotional states (e.g., negative or neutral). The EKG and pneumatic respiration data may be used to filter out the cardiac, respirator, and blood pressure signals on the image sequences to prevent non-emotional systemic HC signals from masking true emotion-related HC signals. Fast Fourier transformation (FFT) may be used on the EKG, respiration, and blood pressure data to obtain the peek frequencies of EKG, respiration, and blood pressure, and then notch filers may be used to remove HC activities on the ROIs with temporal frequencies centering around these frequencies. Independent component analysis (ICA) may be used to accomplish the same goal.

Figure 11:
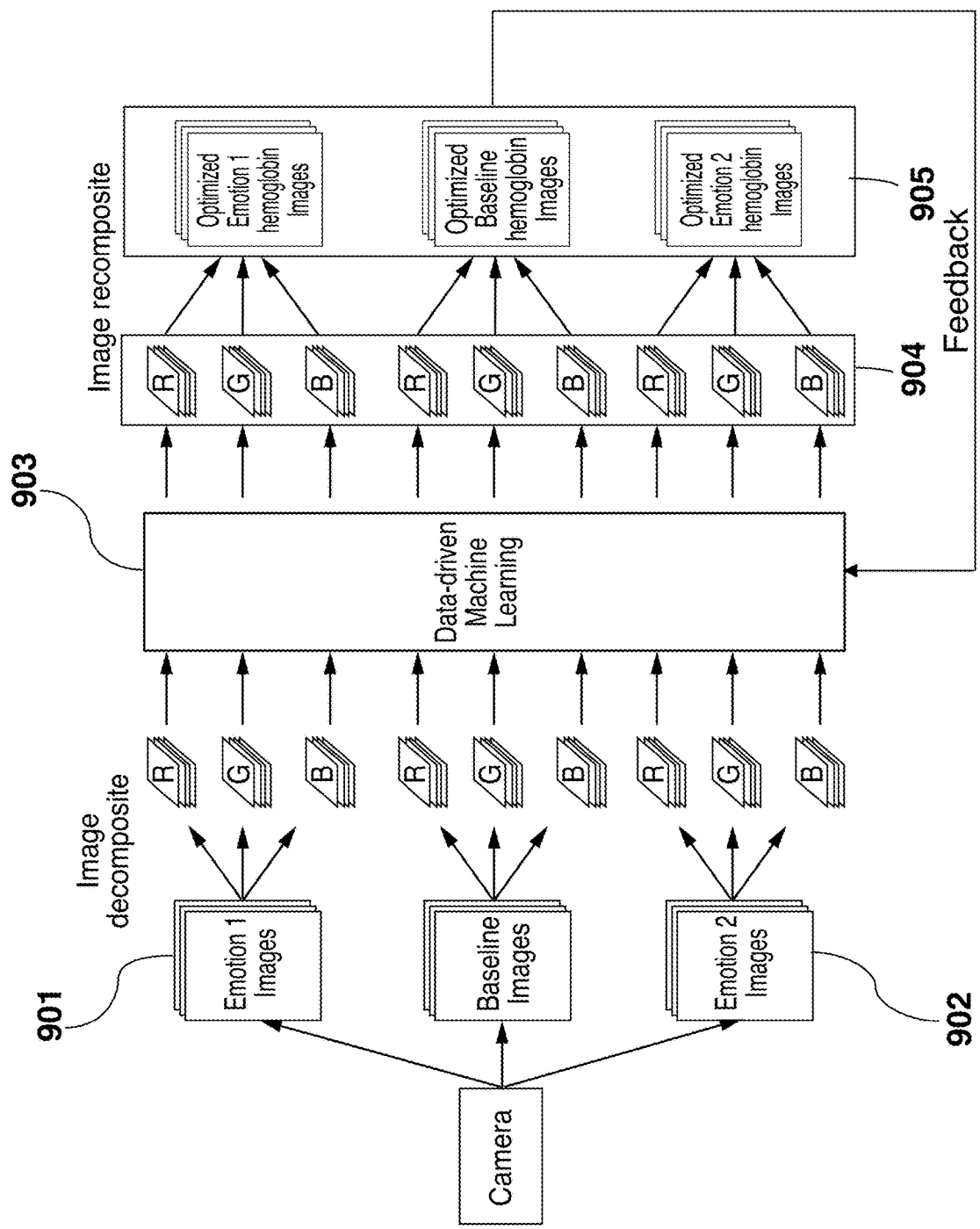
FIG. 11 is an illustration of a data-driven machine learning system for optimized hemoglobin image composition.

Referring now to FIG. 11 an illustration of data-driven machine learning for optimized hemoglobin image composition is shown. Using the filtered signals from the ROIs of two or more than two emotional states 901 and 902, machine learning 903 is employed to systematically identify bitplanes 904 that will significantly increase the signal differentiation between the different emotional state and bitplanes that will contribute nothing or decrease the signal differentiation between different emotional states. After discarding the latter, the remaining bitplane images 905 that optimally differentiate the emotional states of interest are obtained. To further improve SNR, the result can be fed back to the machine learning 903 process repeatedly until the SNR reaches an optimal asymptote.

The machine learning process involves manipulating the bitplane vectors (e.g., 8×8×8, 16×16×16) using image subtraction and addition to maximize the signal differences in all ROIs between different emotional states over the time period for a portion (e.g., 70%, 80%, 90%) of the subject data and validate on the remaining subject data. The addition or subtraction is performed in a pixel-wise manner. An existing machine learning algorithm, the Long Short Term Memory (LSTM) neural network, or a suitable machine trained alternative (such as deep learning) thereto is used to efficiently and obtain information about the improvement of differentiation between emotional states in terms of accuracy, which bitplane(s) contributes the best information, and which does not in terms of feature selection. The Long Short Term Memory (LSTM) neural network or a suitable alternative allows us to perform group feature selections and classifications. The LSTM algorithm is discussed in more detail below. From this process, the set of bitplanes to be isolated from image sequences to reflect temporal changes in HC is obtained. An image filter is configured to isolate the identified bitplanes in subsequent steps described below.

The image classification machine 105 is configured with trained configuration data 102 from a training computer system previously trained with a training set of images captured using the above approach. In this manner, the image classification machine 105 benefits from the training performed by the training computer system. The image classification machine 104 classifies the captured image as corresponding to an emotional state. In the second step, using a new training set of subject emotional data derived from the optimized biplane images provided above, machine learning is employed again to build computational models for emotional states of interests (e.g., positive, negative, and neural).

Figure 12:
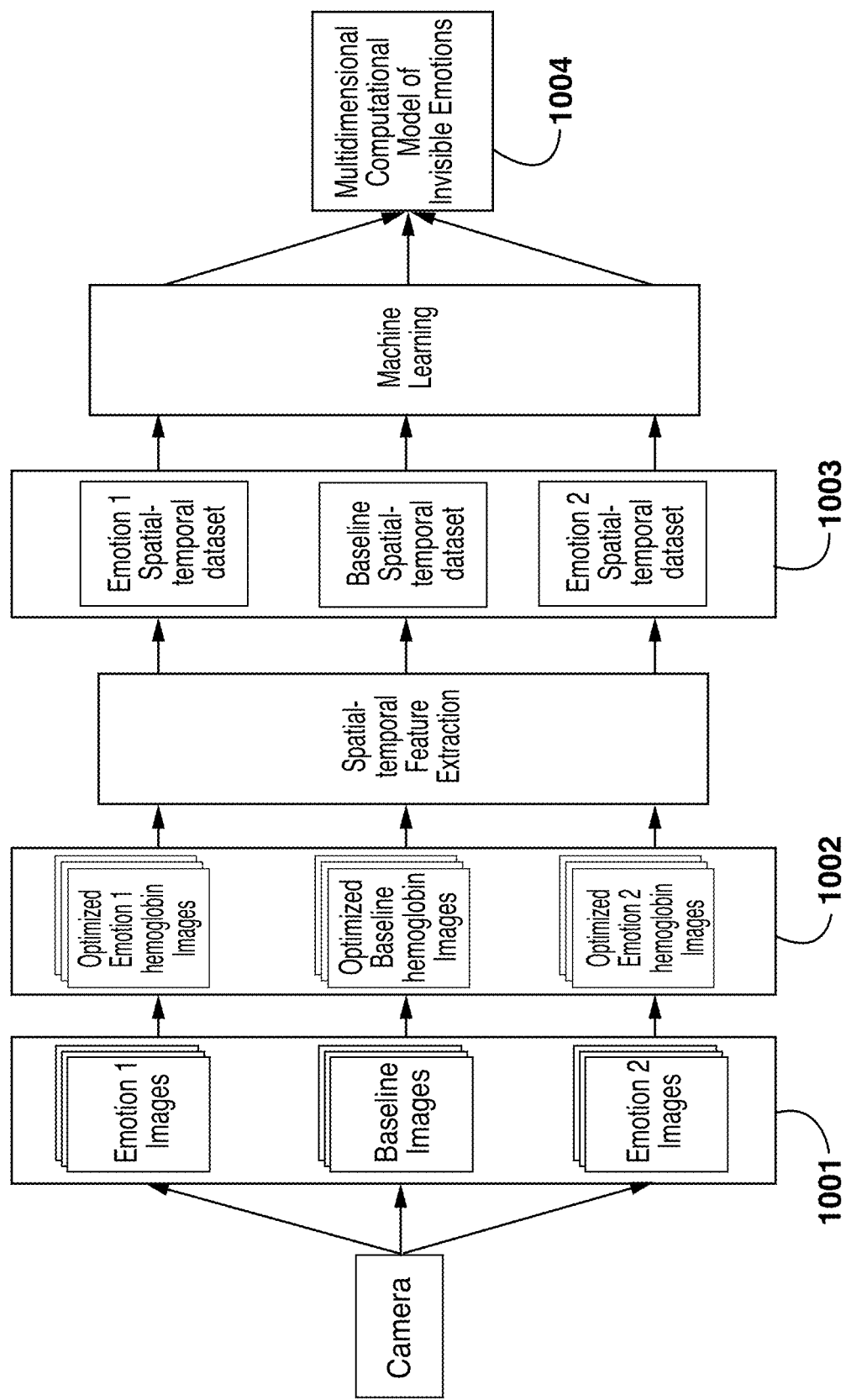
FIG. 12 is an illustration of a data-driven machine learning system for multidimensional invisible emotion model building.

Referring now to FIG. 12, an illustration of data-driven machine learning for multidimensional invisible emotion model building is shown. To create such models, a second set of training subjects (preferably, a new multi-ethnic group of training subjects with different skin types) is recruited, and image sequences 1001 are obtained when they are exposed to stimuli eliciting known emotional response (e.g., positive, negative, neutral). An exemplary set of stimuli is the International Affective Picture System, which has been commonly used to induce emotions and other well established emotion-evoking paradigms. The image filter is applied to the image sequences 1001 to generate high HC SNR image sequences. The stimuli could further comprise non-visual aspects, such as auditory, taste, smell, touch or other sensory stimuli, or combinations thereof.

Using this new training set of subject emotional data 1003 derived from the bitplane filtered images 1002, machine learning is used again to build computational models for emotional states of interests (e.g., positive, negative, and neural) 1003. Note that the emotional state of interest used to identify remaining bitplane filtered images that optimally differentiate the emotional states of interest and the state used to build computational models for emotional states of interests must be the same. For different emotional states of interests, the former must be repeated before the latter commences.

The machine learning process again involves a portion of the subject data (e.g., 70%, 80%, 90% of the subject data) and uses the remaining subject data to validate the model. This second machine learning process thus produces separate multidimensional (spatial and temporal) computational models of trained emotions 1004.

To build different emotional models, facial HC change data on each pixel of each subject's face image is extracted (from Step 1) as a function of time when the subject is viewing a particular emotion-evoking stimulus. To increase SNR, the subject's face is divided into a plurality of ROIs according to their differential underlying ANS regulatory mechanisms mentioned above, and the data in each ROI is averaged.

Figure 7:
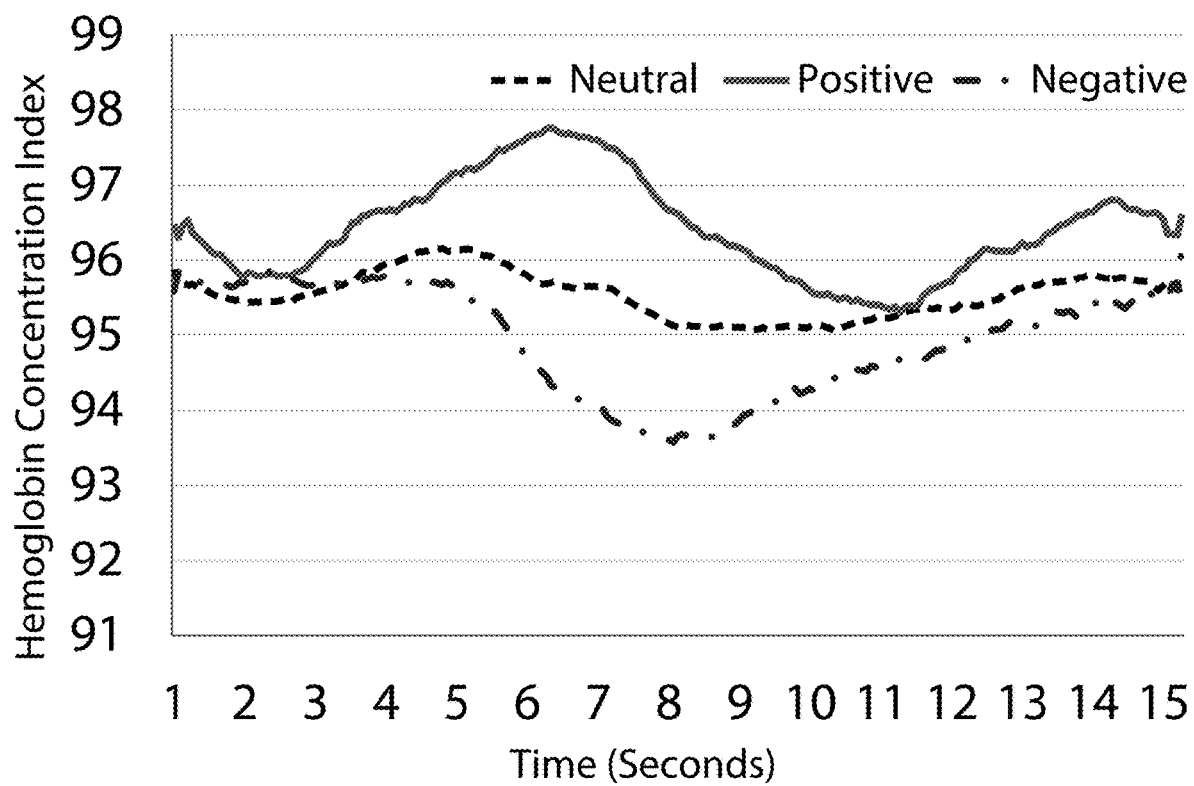
FIG. 7 is a plot illustrating hemoglobin concentration changes for the nose of a subject who experiences positive, negative, and neutral emotional states as a function of time (seconds)
Figure 8:
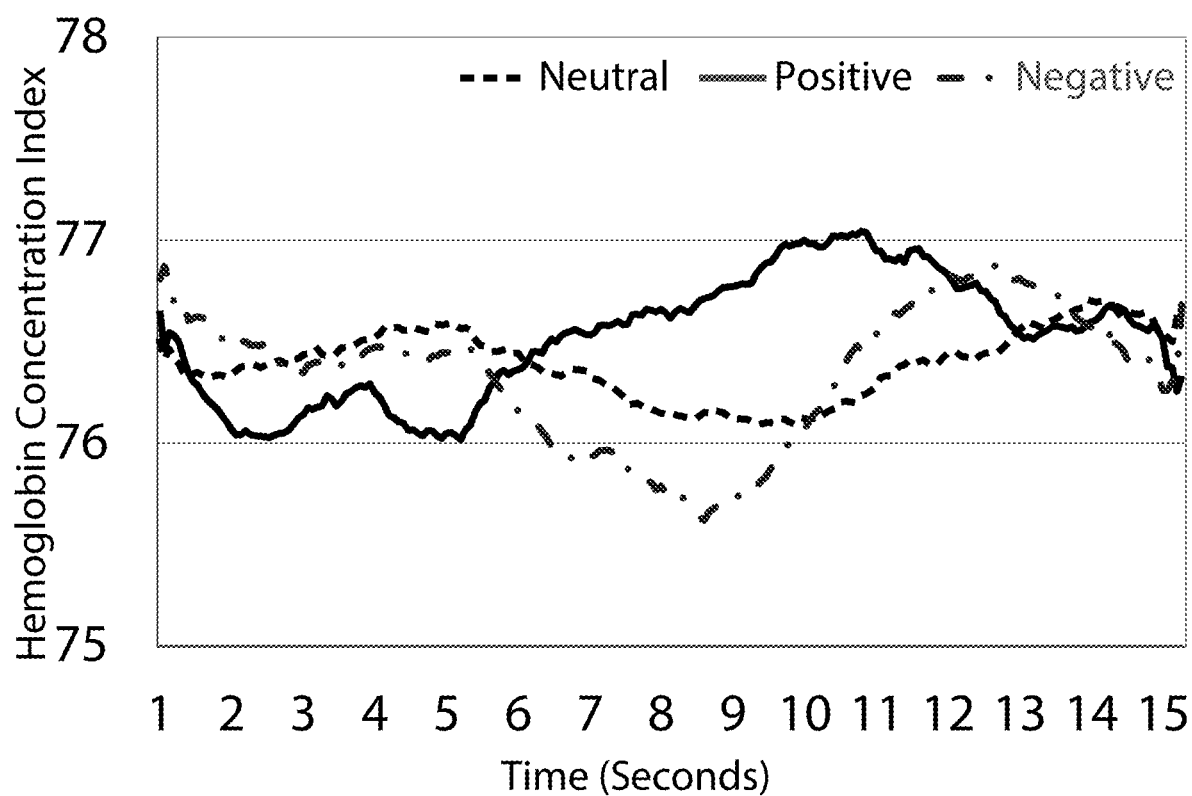
FIG. 8 is a plot illustrating hemoglobin concentration changes for the cheek of a subject who experiences positive, negative, and neutral emotional states as a function of time (seconds)

Referring now to FIG. 4, a plot illustrating differences in hemoglobin distribution for the forehead of a subject is shown. Though neither human nor computer-based facial expression detection system may detect any facial expression differences, transdermal images show a marked difference in hemoglobin distribution between positive 401, negative 402 and neutral 403 conditions. Differences in hemoglobin distribution for the nose and cheek of a subject may be seen in FIG. 7 and FIG. 8 respectively.

The Long Short Term Memory (LSTM) neural network, or a suitable alternative such as non-linear Support Vector Machine, and deep learning may again be used to assess the existence of common spatial-temporal patterns of hemoglobin changes across subjects. The Long Short Term Memory (LSTM) neural network or an alternative is trained on the transdermal data from a portion of the subjects (e.g., 70%, 80%, 90%) to obtain a multi-dimensional computational model for each of the three invisible emotional categories. The models are then tested on the data from the remaining training subjects.

These models form the basis for the trained configuration data 102.

Following these steps, it is now possible to obtain a video sequence from the cameras 32, 38 of any consumer in the retail environment and apply the HC extracted from the selected biplanes to the computational models for emotional states of interest. The output will be (1) an estimated statistical probability that the subject's emotional state belongs to one of the trained emotions, and (2) a normalized intensity measure of such emotional state. For long running video streams when emotional states change and intensity fluctuates, changes of the probability estimation and intensity scores over time relying on HC data based on a moving time window (e.g., 10 seconds) may be reported. It will be appreciated that the confidence level of categorization may be less than 100%.

Two example implementations for (1) obtaining information about the improvement of differentiation between emotional states in terms of accuracy, (2) identifying which bitplane contributes the best information and which does not in terms of feature selection, and (3) assessing the existence of common spatial-temporal patterns of hemoglobin changes across subjects will now be described in more detail. One such implementation is a recurrent neural network.

Figure 14:
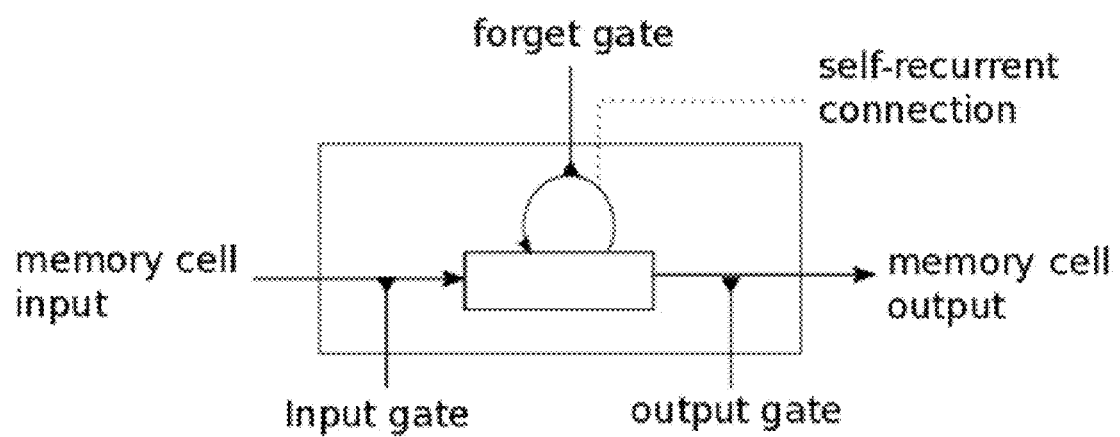
FIG. 14 is a memory cell.

One recurrent neural network is known as the Long Short Term Memory (LSTM) neural network, which is a category of neural network model specified for sequential data analysis and prediction. The LSTM neural network comprises at least three layers of cells. The first layer is an input layer, which accepts the input data. The second (and perhaps additional) layer is a hidden layer, which is composed of memory cells (see FIG. 14). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations:

$x_t$ is the input array to the memory cell layer at time t. In our application, this is the blood flow signal at all ROIs $$\vec{x}_t = [x_{1t} x_{2t} \ldots x_{nt}]'$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t = \sigma(W_i x_t + U_i h_{t-1} + b_i)$$

$$\tilde{C}_t = \tanh(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tanh(C_t)$$

Based on the model of memory cells, for the blood flow distribution at each time step, we can calculate the output from memory cells. Thus, from an input sequence $x_0$, $x_1$, $x_2$, ..., $x_n$, the memory cells in the LSTM layer will produce a representation sequence $h_0$, $h_1$, $h_2$, ..., $h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \text{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

The computer system 34 registers the image streams captured from the various cameras 38, 32 and makes a determination of the invisible emotion detected using the process described above. The detected invisible emotion is then registered with product information, which may comprise a product identifier, the product price displayed, the time that the image sequence was captured, and the length of time that the consumer looked at the products. The computer system 34 can be configured to discard the image sequences upon detecting the invisible emotion.

Referring now to FIG. 10, an exemplary report illustrating the output of the computer system 34 is shown. The computer system 34 registers image sequences by camera, each being associated with a product having a product ID. Each image sequence is analyzed using the process noted above, and is classified as having either a positive (+5.00) or a negative (−5.00) emotional bias, and an intensity (0.00-5.00). These metrics are registered in a database maintained by the computer system 34. The computer system 34 then tallies the results and produces reports upon request, such as the report shown in FIG. 10. The report generated indicates the period for which the results are tallied and statistical metrics for each camera.

Face recognition performed by the computer system can be used to match an image sequence to image sequences previously captured by other cameras to provide a normalized baseline. Further, the locations of the cameras can be registered by the computer system and knowledge of a person's last known location in a retail environment can be used to assist the face recognition performed by the computer system.

In an embodiment, a notification system can be used to provide a notification of an invisible human emotion detected, a face image, and its location. For example, if a consumer reacts positively in front of a particular camera, a sales clerk can be notified and directed to talk to the consumer appearing in the image. Where gaze tracking is determined by the computer system, the notification can also indicate which product a consumer was viewing when the invisible human emotion was detected.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

We claim:

1. A system for determining probability for a state of human emotion among a set of identifiable states of human emotion from a digital image sequence of a person in a retail environment, the system comprising:
   a computer-readable memory comprising the digital image sequence, the digital image sequence being of light re-emitted from the skin of the person before and during viewing of a product; and
   a processing unit comprising one or more processors in communication with the computer-readable memory, the image processing unit executable to:
      determine, using a first machine learning model trained with a hemoglobin concentration (HC) training set, HC changes of the person using bit values from each bitplane of images in the captured image sequence, the HC training set comprising bit values from each bitplane of images captured from one or more people while such people experience a known state of emotion; and
      determine a measure of probability, using a second machine learning model trained with a state training set, for the emotional state of the person against each of the set of identifiable states of human emotion, the state training set obtained by receiving bit values from each bitplane of images representing HC changes determined by the first machine learning model.

2. The system of claim 1, wherein determining the measure of probability, using the second machine learning model trained with the state training set, for the emotional state of the person further comprises determining a normalized intensity measure for the emotional state.

3. The system of claim 1, wherein the person views the product before and during a point of sale event comprising a price display device displaying a price.

4. The system of claim 3, wherein the point of sale event comprises the price display device temporarily displaying a discounted price.

5. The system of claim 3, wherein the captured image sequence is received from a camera that is integral to the price display device.

6. The system of claim 5, further comprising a motion sensor to detect motion in a region proximal the product display, and to, upon detecting motion in the region, trigger the camera to capture the image sequence and the price display device to display the price.

7. The system of claim 5, wherein the processing unit is configured to receive locations of the camera and the product, to perform gaze tracking to analyze the image sequence to determine whether the person is looking at the product during the point of sale event, and to discard the image sequence if the person is not looking at the product during the point of sale event.

8. The system of claim 1, further comprising outputting of the detected emotional state with the highest measure of probability to a display.

9. A method for determining probability for a state of human emotion among a set of identifiable states of human emotion from a digital image sequence of a person in a retail environment, the digital image sequence being of light re-emitted from the skin of the person before and during viewing of a product, the method comprising:
   determining, using a first machine learning model trained with a hemoglobin concentration (HC) training set, HC changes of the person using bit values from each bitplane of images in the captured image sequence, the HC training set comprising bit values from each bitplane of images captured from one or more people while such people experience a known state of emotion; and
   determinizing a measure of probability, using a second machine learning model trained with a state training set, for the emotional state of the person against each of the set of identifiable states of human emotion, the state training set obtained by receiving bit values from each bitplane of images representing HC changes determined by the first machine learning model.

10. The method of claim 9, wherein determining the measure of probability, using the second machine learning model trained with the state training set, for the emotional state of the person further comprises determining a normalized intensity measure for the emotional state.

11. The method of claim 9, wherein the person views the product before and during a point of sale event comprising a displaying a price.

12. The method of claim 11, wherein the point of sale event comprises temporarily displaying a discounted price.

13. The method of claim 11, further comprising detecting motion in a region proximal the product, and, upon detecting motion in the region, capturing the image sequence and displaying the price.

14. The method of claim 11, further comprising performing gaze tracking to analyze the image sequence to determine whether the person is looking at the product during the point of sale event, and discarding the image sequence if the person is not looking at the product during the point of sale event.

15. The method of claim 9, further comprising outputting of the detected emotional state with the highest measure of probability.

\* \* \* \* \*